United States Patent [19]

Mack, Jr. et al.

[11] 4,218,421
[45] Aug. 19, 1980

[54] DISPOSABLE CONTAINER FOR A CONTINUOUS BAND OF TEST STRIPS

[75] Inventors: John C. Mack, Jr.; Dean M. Peterson, both of Littleton, Colo.

[73] Assignee: Honeywell Inc., Minneapolis, Minn.

[21] Appl. No.: 935,031

[22] Filed: Aug. 18, 1978

[51] Int. Cl.$^2$ .................... G01N 33/16; G01N 31/00; G01N 1/10
[52] U.S. Cl. ..................................... 422/66; 422/102; 422/56
[58] Field of Search ............... 422/66, 102, 61, 56; 141/130; 73/421 R, 425.4 R; 221/197

[56] References Cited

U.S. PATENT DOCUMENTS

| | | | |
|---|---|---|---|
| 3,216,804 | 11/1965 | Natelson | 422/66 |
| 3,554,005 | 1/1971 | Koblin et al. | 422/66 |
| 3,675,488 | 7/1972 | Viktora et al. | 422/66 |
| 3,728,081 | 4/1973 | Bidanset | 422/66 |
| 3,904,369 | 9/1975 | Adler et al. | 422/66 |

Primary Examiner—R. E. Serwin
Attorney, Agent, or Firm—Charles G. Mersereau

[57] ABSTRACT

An apparatus for storing and dispensing a continuous band of medical reagent test strips is disclosed which includes chambers for the storage of used and unused portions of the continuous strip separated by barrier member to prevent cross-contamination there between. A substantially flat interim space is provided between the accesses to the chambers wherein tests may be run utilizing the samples in conjunction with the strips. Mechanical means is provided for advancing the band of medical test strips as necessary. The apparatus may be fabricated of suitable, moldable plastic material which may be discarded after the band of unused medical reagent test strips is exhausted.

5 Claims, 4 Drawing Figures

DISPOSABLE CONTAINER FOR A CONTINUOUS BAND OF TEST STRIPS

BACKGROUND OF THE INVENTION

1. Field of the Invention

The present invention relates generally to the field of automated biological testing and, more particularly, it relates to a device for housing dispensing continuous bands of space chemical reagent test strips to which samples are applied in the testing of biological specimens.

2. Description of the Prior Art

In the prior art, segmented reagent test strips have been used for in vitro diagnostics to run several tests on a given specimen simultaneously. Such test strips having a plurality of test pads, each of which is treated with a different chemical reagent have been used to test biological specimens such as urine. Each pad and its associated chemical reagent is used to make a different chemical determination from a given sample. The reactions normally take less than a minute and the results are presented by a color change in the pad, which change can be detected optically.

Present means for housing urine chemistry test strips and the like involve the use of bottles, cans, boxes and other such containers which serve to prevent the chemical reagents on the strip pads from becoming contaminated or decomposing due to exposure to external contaminants. The strips are individually removed from the container and dipped in the sample by hand. To contamination problems and storage problems, this adds the possible problems associated with the technician contacting either the specimen or the pads directly, thus, interfering with the test results.

SUMMARY OF THE INVENTION

In accordance with the present invention the problems associated with the storage and dispensing of chemical reagent test strips is solved by the use of a special disposable storage and dispensing container. The container uses the medical chemical test strips in the form of a continuous band of such strips. The present invention contemplates a disposable container having juxtaposed hollow inner chambers which may be cylindrically shaped. One such chamber, called the storage chamber, is designed to contain the unused portion of the continuous band of reagent test strips. The other chamber, a take-up chamber, is utilized to store the used portion of the continuous band of reagent test strips. The chambers are separated from each other by a barrier member to prevent cross contamination between used and unused strips. The chambers communicate with the outside through narrow elongated channels or slots. The continuous band is mounted such that it extends out of the storage chamber and into the take-up chamber. A substantially flat, smooth area separates the slots which is used as a sample testing and strip reading surface.

The take-up chamber is further provided with a take-up reel or spool which has an associated sprocket which may be operated manually or connected to a motorized conventional mechanical system. This take-up reel is used to connect used test strips or winding same about the reel.

The test strips used in the apparatus could be any desired conventional chemical reagent test strips which have been placed side by side and connected by a webbing or tape such that successive strips and spacings there between be used for the continuous band.

The container is normally formed in two parts, a housing, and a cover. The housing defines the internal storage and take-up chambers. The storage chamber may be loaded with the desired amount of test strip band and the leading portion of the band threaded from the storage chamber across the testing and reading surface, into the take-up chamber and linked to the take-up reel in conventional fashion. After loading, the cover is provided which completes the housing and may be permanently affixed in place.

The entire apparatus can be placed in a large test instrument wherein a plurality of tests are run on specimens on each strip in automated fashion. The number of possible tests corresponding to the number of pads present on each strip.

In operation, the band of test strips is advanced an amount equal to that necessary to position one strip at a given point on the sample testing and reading surface for testing. After the test is conducted on that particular strip, the next strip can then be advanced to the same place.

BRIEF DESCRIPTION OF THE DRAWINGS

In the drawings wherein like numerals are utilized to designate like parts throughout the same.

DESCRIPTION OF THE PREFERRED EMBODIMENT

Figure 1:
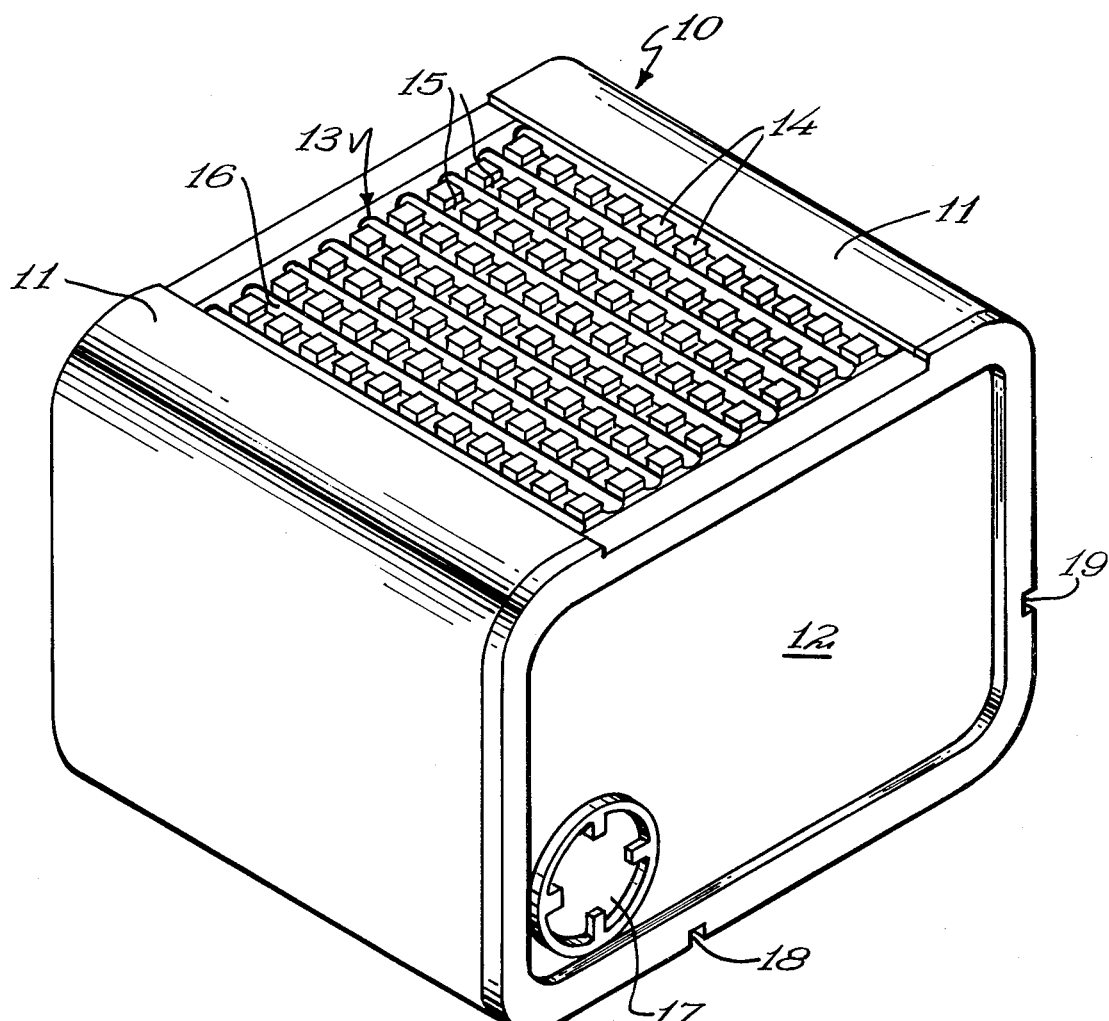
FIG. 1 is a perspective view of the chemical reagent test strip storage and dispensing apparatus of the invention.

In FIG. 1 there is shown generally at 10 the storage and dispensing apparatus for a continuous band of chemical reagent test strips of the invention. This includes a main body or housing member 11 and an associated closure or cover member 12.

A continuous band of medical test strips is shown at 13 including a plurality of chemcial reagent test pads 14 mounted on the strips 15 which are, in turn, fastened together as by a webbing or tape 16 to form a continuous band. Each of the pads 14 associated with each given strip 15 is impregnated with a different chemical reagent such that when all the pads on a given strip are contacted by a biological sample such as a urine sample, a plurality of chemical tests may be conducted in a given sample simultaneously. In the illustration of FIG. 1, each of the test strips 15 contains eleven of the pads 14. Of course, if more or fewer tests are desired the number of pads 14 per strip 15 can then be varied as desired.

The drive sprocket 17 associated with a take-up reel, discussed in more detail in conjunction with FIG. 2, below, and alignment or orientation slots 18 and 19 are also provided. The slots 18 and 19 are associated with raised keys in the alignment of the storage and dispensing apparatus when used in conjunction with a larger medical testing device.

Figure 2:
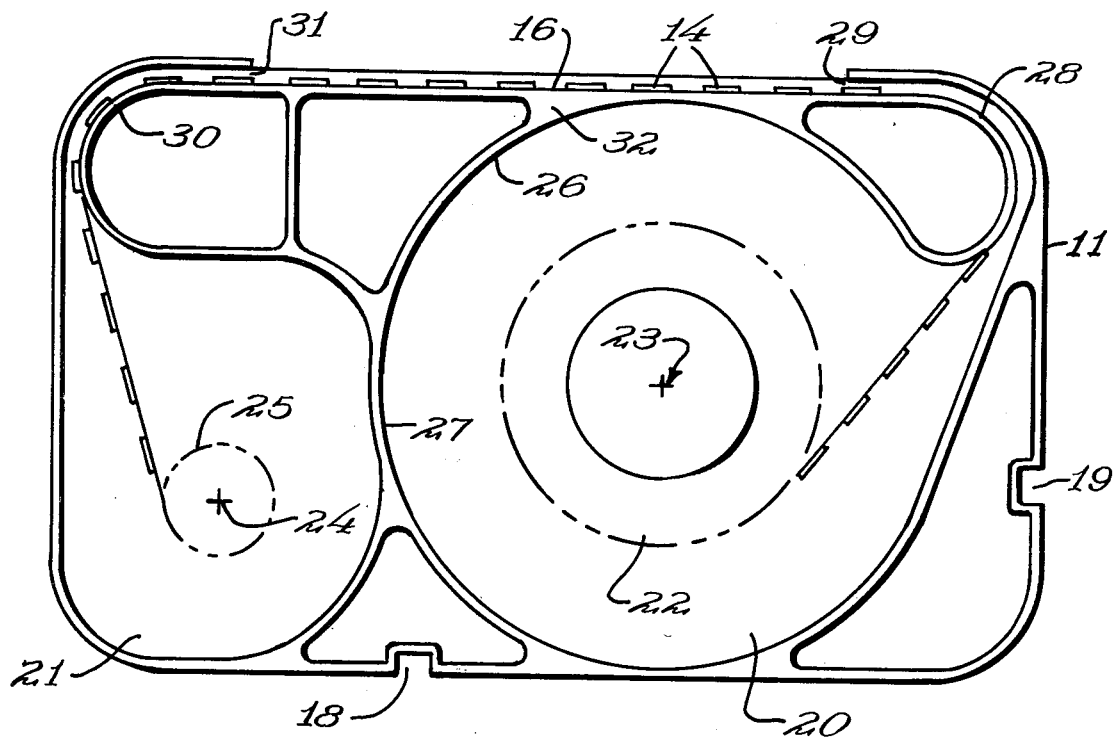
FIG. 2 is an end view of the apparatus of FIG. 1 with the cover removed.

FIG. 2 depicts the apparatus of FIG. 1 with the end or cover member 12 thereof removed exposing the interior details. The housing member 11 defines a chamber for unused reagent test strips called a storage chamber 20 and a chamber for the retention of used reagent test strips or a take-up chamber 21. The chambers are elongated and may be substantially cylindrical in shape. The length of the cylinder is dependent on the length of the reagent test strips 15 and the diameter, of course, being dependent upon the number of strips desired to be stored in a given arrangement. The quantity of the band of unused chemical reagent test strip material is shown in phantom at 22 basically wrapped around a spool, the center of which is shown at 23. The center of the take-up spool is designated 24 and the quantity of used test strip material is designated by the phantom line 25 in the chamber 21.

The chambers 20 and 21 are defined as is the path of the band of test strips 16 by a series of structural webs as at 26. The web portion at 27 separates chambers 20 and 21 and to prevent any possible cross-contamination between the chambers 20 and 21. The webs or the like are actually in the form of internal walls which extend for the entire depth of the member 11. The internal wall 28 guides the strip 16 along the exit path from the chamber 20 through the exit channel or slot 29. In similar fashion, the wall portion 30 guides the band 16 into the chamber 21 through the entry channel or slot 31.

The internal structure of the housing members of the container 11 is designed such that the member is structurally rigid in addition to providing the necessary chambers and the desirable type channels for guiding the band 16 in its path about the container. The exit channel slot 29 is designed to allow free passage of the strips out of the channel but without protrusions of any kind which might hinder passage of the band 16 or catch any of the pads 14 to cause any damage to the reagent pad. Likewise, the entry slot or channel 31 must be constructed such that the strips do not bind or are hindered when passing into the chamber 21.

That portion of the housing or container structure dubbed 32 defines a substantially flat, smooth platen area over which the band of test strips 16 passes between the channel 29 and the channel 31. This area is utilized for sample testing and result reading. It must provide a flat support for the test strip in order that accurate results may be achieved from the testing process.

The take-up reel 24 is designed so that the used portion of the band of chemical reagent test strips is collected by winding the strips tightly on the reel so that used strips are isolated in a reduced volume to prevent contaminants or noxious odors from emanating through the channel 31 insofar as such is possible.

Figure 3:
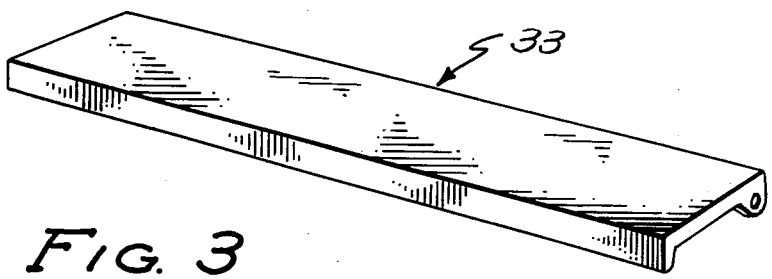
FIG. 3 is an enlarged perspective view of a protective cover associated with the storage chamber of the apparatus.
Figure 4:
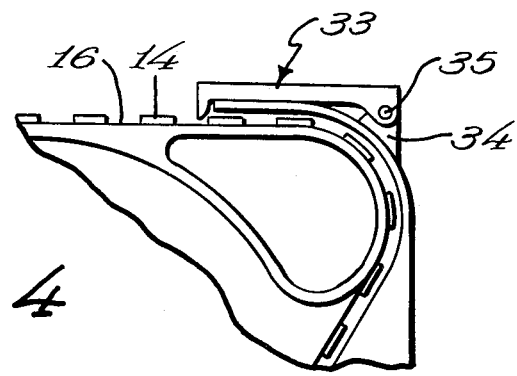
FIG. 4 is an enlarged fractional view of a portion of the apparatus of FIG. 2 showing a protective cover in place.

It should be noted that the supply of unused chemical reagent test strip material 22 may be internally provided with a desiccant dryer, if desired, or other such material as is necessary to aid in the preservation of the freshness of the reagent contained on the pads 14 during the storage thereof. In addition, as shown in the perspective view of FIG. 3 and also in conjunction with the enlarged fragmentary view of FIG. 4, there may be provided a housing cover 33 pivotally attached to ears as at 34 by means of conventional hinge pins as shown at 35. This cover aids in preventing any outside contaminant materials from traversing with the slot or channel 29 in reaching the unused test strips contained in the chamber 20. The member 33 very loosely hinged on the pins 35 such that the motion of the band of test strips 16 through the opening 29 causes the number 33 to raise up or ride over the pads 14 without binding, hindering or damaging them.

In producing the disposable medical chemical test strip dispensing and storage apparatus of the present invention, while any suitable material may be used the parts are preferably made of a suitable moldable plastic material. Thus the main housing member 11 may be molded as a single piece from a plastic which has the suitable molding characteristics along with the characteristic of chemical inertness to the reagent utilized in the chemical reagent test strips. This is to assure that there is no cross contamination between the test strips and the material of the container. Such materials as polyethelene or polystyrene are normally suitable for such construction. Likewise, the sealing or cover section 12 may also be a single molded piece. The take-up reel 24 and a dispensing wheel, if desired, may also be a plastic or a suitable metallic composition.

In the assembly of the device, the continuous band of test strip material is placed in the chamber 20 and threaded through the opening 29 across to the opening 31 and attached to the rewind or take-up reel 24 either using a slot or other connectional fastening means such as taping. This is accomplished prior to the placing of the enclosure or cover number 12 over the assembly. The initial portion of the band of chemical reagent test strips may be a leader portion without the strips attached, if desired, such that none of the strips will be wasted and cannot be used for testing. The cover may then be permanently fixed in place with the test strip material ready to be advanced by the sprocket 17 which, at the time that the cover 12 is placed on the housing member 11, may also fix itself to the take-up reel 24. The openings 29 and 31 may then be sealed for shipment by the use of suitable tape or other sealing means to preserve the integrity of the chemical testing material prior to the actual use of the material for testing.

In operation, the entire assembly is normally slid into place on a test module utilizing the orientation slots 18 and 19. The continuous band 16 may be provided with markings adjacent each of the chemical reagent test strips 15 which correspond to markings on the housing of the device such that each strip may be properly aligned at each necessary position along the surface 32. In this manner as the continuous band 16 is advanced, upon reaching a designated station on the surface 32, a sample is applied across the entire width of a given test strip 15 such that a portion of the specimen is placed on each of the several pads 14. After the continuous band 16 is advanced either manually or automatically a given number of stations, the reagent has had a chance to react with the specimen sample and the result may be read optically. The strip then advanced on into the take-up chamber 21. In this fashion, several hundred tests may be run utilizing a single band of materials supplied to the chamber 20.

When all the test strips have been used and the entire band has been advanced into the chamber 21, the entire cassette may be removed and discarded in the manner of a spent cartridge and replaced by a fresh unit. The ease and frugality achieved in the construction of the unit allows it to be readily disposable. It also may readily be appreciated that any tension required in maintaining the continuous band 16 in position may be provided by the utilization of one or more tension springs either in connection with the take-up reel 24 or a dispensing reel 23 in highly conventional fashion.

The embodiments of the invention in which an exclusive property or right is claimed are defined as follows:

1. A self-contained, disposable cartridge unit for storing and dispensing a continuous band of chemical reagent test strips for use with the chemical analyzing apparatus, said cartridge unit comprising:

a first chamber for containing the unused portion of said band of test strips in substantially coil form;

a second chamber for containing the used portion of said band of test strips in substantially coil form;

barrier means in said cartridge unit internally isolating said second chamber from said first chamber;

oppositely facing spaced slotted openings in said first and said second chambers to permit the passage of said band of test strips from said first to said second chamber;

integral fixed platen for continuously supporting said band of said test strips between said first and second chambers wherein the addition of specimens to said test strips and the testing thereof may take place;

a single, drivable take-up reel associated with said second chamber having a sprocket adapted to be externally driven; and alignment slots for positioning said disposable cartridge unit in said chemical analyzing unit.

2. The apparatus of claim 1 wherein an extension of said platen provides a substantially smooth curve exit channel for said first chamber for the protection of exiting unused strips.

3. The apparatus of claim 1 further comprising closure means associated with said slotted openings to prevent contamination of said test strips when not in use.

4. The apparatus of claim 1 including means for positioning said strips in said band in said intervening space.

5. The apparatus of claim 4 including a desiccant ascociated with the volume of said first chamber to preserve said unused strips.

* * * * *